United States Patent
Kloeppel

[11] Patent Number: 5,865,174
[45] Date of Patent: Feb. 2, 1999

[54] SUPPLEMENTAL OXYGEN DELIVERY APPARATUS AND METHOD

[75] Inventor: Gregg M. Kloeppel, Sheffield Lake, Ohio

[73] Assignee: The Scott Fetzer Company, Westlake, Ohio

[21] Appl. No.: 738,583

[22] Filed: Oct. 29, 1996

[51] Int. Cl.⁶ ................................................ A61M 16/00
[52] U.S. Cl. ............................ 128/204.23; 128/204.26; 128/207.18; 128/204.21
[58] Field of Search ................... 128/204.18, 204.21, 128/204.23, 204.26, 205.23, 202.22, 207.18

[56] References Cited

U.S. PATENT DOCUMENTS

| | | |
|---|---|---|
| 3,333,584 | 8/1967 | Andreasen et al. . |
| 3,357,428 | 12/1967 | Carlson . |
| 3,659,598 | 5/1972 | Peters et al. . |
| 3,736,949 | 6/1973 | Wolter et al. . |
| 3,834,382 | 9/1974 | Lederman et al. . |
| 3,889,669 | 6/1975 | Weigl . |
| 3,910,270 | 10/1975 | Stewart . |
| 3,952,740 | 4/1976 | Scurlock . |
| 4,054,133 | 10/1977 | Myers . |
| 4,057,059 | 11/1977 | Reid, Jr. et al. . |
| 4,106,503 | 8/1978 | Rosenthal et al. . |
| 4,120,300 | 10/1978 | Tiep . |
| 4,141,354 | 2/1979 | Ismach . |
| 4,141,356 | 2/1979 | Smargiassi . |
| 4,206,754 | 6/1980 | Cox et al. .......................... 128/204.21 |
| 4,281,651 | 8/1981 | Cox .................................... 128/204.23 |
| 4,289,142 | 9/1981 | Kearns .................................... 128/716 |
| 4,316,182 | 2/1982 | Hodgson ................................ 340/606 |
| 4,323,064 | 4/1982 | Hoenig et al. ..................... 128/204.23 |
| 4,331,455 | 5/1982 | Sato ........................................... 55/21 |
| 4,381,774 | 5/1983 | Schreiber ........................... 128/202.22 |
| 4,414,982 | 11/1983 | Durkan .................................... 128/716 |
| 4,457,303 | 7/1984 | Durkan .............................. 128/204.24 |
| 4,461,293 | 7/1984 | Chen .................................. 128/204.23 |
| 4,462,398 | 7/1984 | Durkan et al. ..................... 128/200.14 |
| 4,484,578 | 11/1984 | Durkan .............................. 128/204.24 |
| 4,506,666 | 3/1985 | Durkan .............................. 128/204.23 |
| 4,519,387 | 5/1985 | Durkan et al. ..................... 128/204.23 |
| 4,570,631 | 2/1986 | Durkan .............................. 128/204.23 |
| 4,612,928 | 9/1986 | Tiep et al. ......................... 128/204.23 |
| 4,648,395 | 3/1987 | Sato et al. ......................... 128/204.23 |
| 4,681,099 | 7/1987 | Sato et al. ......................... 128/204.23 |
| 4,686,974 | 8/1987 | Sato et al. ......................... 128/204.23 |
| 4,686,975 | 8/1987 | Naimon et al. .................... 128/204.23 |

(List continued on next page.)

FOREIGN PATENT DOCUMENTS

| | | |
|---|---|---|
| 0657182 | 11/1993 | European Pat. Off. . |
| 9616591 | 11/1994 | WIPO . |

*Primary Examiner*—Aaron J. Lewis
*Attorney, Agent, or Firm*—Jones, Day, Reavis & Pogue

[57] ABSTRACT

An apparatus conserves oxygen delivered from a supply (28) to a patient through a cannula (44) by providing oxygen delivery selectively in accordance with the physiological requirements and current breathing pattern of the patient. Oxygen flow is set at a prescribed flow rate from the supply by a regulator (30). An oxygen conserving unit (38) includes a controller (64) that operates responsive to timed relationships among pressure signals determined by a fuzzy logic program to deliver oxygen to the patient by opening a valve (72) when a sensed pressure in the patient's nasal passage reaches a threshold level and when the controller determines that the reaching of the threshold is indicative of an inhalation cycle. The controller is further operative to adjust the time period that oxygen is delivered to the patient in accordance with a programmed relation to meet the dynamically changing needs of the patient. The apparatus further includes features which provide fast response, conservation of the energy from a battery power source (86) and both visual and audio indicators (54, 56) to provide indications of alert and alarm conditions. The apparatus further provides control by the user through a single manually actuated switch (52), and mechanical interconnection with the switch and valve to assure continuous flow when the switch is set to a continuous flow setting.

54 Claims, 8 Drawing Sheets

U.S. PATENT DOCUMENTS

| | | | |
|---|---|---|---|
| 4,706,664 | 11/1987 | Snook et al. | 128/204.23 |
| 4,779,446 | 10/1988 | Rowland | 73/1 R |
| 4,803,471 | 2/1989 | Rowland | 340/626 |
| 4,957,107 | 9/1990 | Sipin | 128/204.18 |
| 4,986,269 | 1/1991 | Hakkinen | 128/204.23 |
| 4,989,599 | 2/1991 | Carter | 128/207.18 |
| 4,990,894 | 2/1991 | Loescher et al. | 340/573 |
| 5,024,219 | 6/1991 | Dietz | 128/204.21 |
| 5,038,771 | 8/1991 | Dietz | 128/204.21 |
| 5,074,299 | 12/1991 | Dietz | 128/204.21 |
| 5,099,836 | 3/1992 | Rowland et al. | 128/204.23 |
| 5,134,886 | 8/1992 | Ball | 73/718 |
| 5,150,291 | 9/1992 | Cummings et al. | 364/413.03 |
| 5,161,525 | 11/1992 | Kimm et al. | 128/204.26 |
| 5,165,397 | 11/1992 | Arp | 128/204.21 |
| 5,211,170 | 5/1993 | Press | 128/204.23 |
| 5,303,700 | 4/1994 | Weismann et al. | 128/204.23 |
| 5,365,922 | 11/1994 | Raemer | 128/204.23 |
| 5,388,575 | 2/1995 | Taube | 128/204.23 |
| 5,490,502 | 2/1996 | Rapoport et al. | 128/204.23 |
| 5,503,146 | 4/1996 | Froehlich et al. | 128/204.23 |
| 5,577,496 | 11/1996 | Blackwood et al. | 128/204.23 |
| 5,603,315 | 2/1997 | Sasso, Jr. | 128/204.18 | ns
SUPPLEMENTAL OXYGEN DELIVERY APPARATUS AND METHOD

TECHNICAL FIELD

This invention relates to devices and methods for delivering supplemental oxygen to patients who suffer from respiratory conditions. Specifically, this invention relates to an apparatus and method for conserving a supply of oxygen while providing a patient with a therapeutic equivalent of a continuous flow of oxygen.

BACKGROUND ART

Persons with certain respiratory conditions receive therapeutic benefits from having supplemental oxygen delivered to their respiratory passages while breathing air from the atmosphere. This supplemental oxygen serves to increase the amount of oxygen delivered to the patient's body tissue through the blood stream. This is accomplished because the supplemental oxygen increases the patient's $SaO_2$ level which is the measure of oxygen saturated hemoglobin in the blood.

The conventional approach to providing supplemental oxygen to a patient is schematically shown in FIG. 1. This prior art system generally designated 10, includes a supply of oxygen 12. In the embodiment shown, the supply is a portable oxygen supply such as a pressurized oxygen bottle. A flow rate controlling regulator 14 is positioned on the supply 12 and is in fluid communication therewith. Regulator 14 may be a pressure compensated regulator of the type known in the prior art which includes an adjustment member 16 thereon. Adjustment member 16 is adjustable to change the rate of flow from the supply into an oxygen delivery line 18. Oxygen delivery line 18 is in fluid communication with a cannula 20. Cannula 20 includes a pair of passages 22 each of which communicates with a nasal passage 24 of a patient which is shown in phantom.

In conventional oxygen therapy the physiological characteristics of the patient are studied to determine a continuous flow rate of supplemental oxygen that proves beneficial to the patient. Regulator 14 is set to deliver this prescribed flow rate by positioning adjustment member 16. The oxygen is continuously delivered at this prescribed flow rate through the cannula 20 to the patient's nasal passages.

A drawback associated with conventional oxygen therapy is that the patient only benefits from the supplemental oxygen during times in the respiratory cycle when the patient is inhaling in a manner which enables the supplemental oxygen to reach the lungs. At other times the supplemental oxygen delivered is of no benefit, and is lost.

Continuous delivery of oxygen presents a drawback when the patient is using a portable oxygen supply with a limited capacity. When oxygen is delivered continuously the time period the patient may use the portable oxygen supply is limited to the capacity of the supply divided by the prescribed flow rate. The capacity available from a reasonably sized oxygen bottle or other supply may not enable a patient to use a single portable supply for as long as would be desirable.

Others have previously developed oxygen conserving devices to extend the time that a patient may receive oxygen before depleting a supply. These prior approaches generally have drawbacks.

Certain oxygen conserving devices attempt to deliver a fixed pulse of oxygen to a patient at the start of inspiration in each respiratory cycle. However, as a patient's activity level increases, the fixed pulse of oxygen may be insufficient to maintain the patient's blood oxygen level. The patient may have a tendency to desaturate, meaning that their $SaO_2$ level falls below a patient's required oxygen saturation level.

As a patient's exertion level changes, breathing patterns may also change. Prior oxygen conserving devices rely for their beneficial affect on detecting the beginning of a patient's inhalation or inspiration during each respiratory cycle. Because breathing patterns can become irregular, prior devices often fail to properly detect the optimum point in the respiratory cycle for the delivery of the supplemental oxygen. This can result in desaturation of the patient's blood oxygen level because oxygen is being delivered at inappropriate times. Often during irregular breathing prior devices deliver pulses of oxygen at a frequency that is much higher than the actual breathing rate of the patient. Much of the supplemental oxygen can be wasted when the breathing pattern becomes irregular.

Certain previously developed supplemental oxygen delivery devices deliver a burst of oxygen into a patient's nasal passages when a patient begins to inhale. This burst of oxygen is often uncomfortable for the patient. In addition, such high flow pulses generally cannot be tailored to the patient's physiological requirements or dynamically adjusted to meet the needs of the patient's changing activity level or breathing pattern.

Thus, there exists a need for a supplemental oxygen delivery apparatus and method that conserves oxygen while providing the patient with a therapeutic equivalent of continuous oxygen flow, and which overcomes the drawbacks associated with prior conserving devices.

DISCLOSURE OF INVENTION

It is an object of the present invention to provide an apparatus for delivering supplemental oxygen to a patient.

It is a further object of the present invention to provide an oxygen conserving apparatus.

It is a further object of the present invention to provide an oxygen conserving apparatus that provides a patient with a physiological equivalent of continuous oxygen flow at a prescribed rate.

It is a further object of the present invention to provide an oxygen conserving apparatus that extends the time that a portable oxygen supply may be used by a patient.

It is a further object of the present invention to provide an oxygen conserving apparatus that more accurately meets the physiological requirements of a patient.

It is a further object of the present invention to provide an oxygen conserving apparatus that is more comfortable for a patient to use.

It is a further object of the present invention to provide an oxygen conserving apparatus that more accurately delivers oxygen at a therapeutically beneficial point in a patient's respiration cycle.

It is a further object of the present invention to provide an oxygen conserving apparatus that is reliable, portable, compact and easy to operate.

It is a further object of the present invention to provide an oxygen conserving apparatus that provides an indication of its proper operation.

It is a further object of the present invention to provide an oxygen conserving apparatus that provides an indication of a condition of its battery power source during each respiration cycle.

It is a further object of the present invention to provide an oxygen conserving apparatus that provides an indication if it is not properly sensing a patient's respiration.

It is a further object of the present invention to provide an oxygen conserving apparatus which defaults to a fail safe mode in which oxygen is continuously supplied to a patient.

It is a further object of the present invention to provide an oxygen conserving apparatus that may be changed between a conserve mode and a mode in which continuous prescribed flow is provided, by movement of a single manually actuated switch.

It is a further object of the present invention to provide an oxygen conserving apparatus that when manually changed to the continuous flow mode, mechanically assures that flow therethrough is enabled.

It is a further object of the present invention to provide an oxygen conserving apparatus that detects and indicates irregularities in a patient's respiration.

It is a further object of the present invention to provide a method for delivering supplemental oxygen to a patient.

It is a further object of the present invention to provide a method for delivering supplemental oxygen to a patient while conserving oxygen delivered from a supply.

It is a further object of the present invention to provide a method for delivering supplemental oxygen to a patient through an oxygen conserving device which tailors the amount of oxygen delivered to the patient to the patient's physiological requirements and changing oxygen needs.

It is a further object of the present invention to provide a method for delivering supplemental oxygen to a patient that more reliably delivers oxygen at times during respiration cycles when the supplemental oxygen provides greater therapeutic benefits.

It is a further object of the present invention to provide a method for delivering supplemental oxygen to a patient through a conserving apparatus that is easy to use, indicates proper operation, indicates irregular conditions in a patient's respiration, and which defaults to a fail safe condition.

Further objects of the present invention will be made apparent in the following Best Modes for Carrying Out Invention and the appended claims.

The foregoing objects are accomplished in a preferred embodiment of the present invention by an oxygen conserving apparatus and method which delivers oxygen from an oxygen supply to a nasal passage of a patient. The apparatus operates to conserve oxygen to extend the life of the supply while providing the patient with therapeutic benefits comparable to a continuous flow of oxygen.

The conserving apparatus includes a sensing passage which is fluidly connectable to a nasal passage of a patient. The apparatus further includes a delivery passage separated from the sensing passage and which is also fluidly connectable to the nasal passage of the patient. The apparatus includes a pressure sensor which senses a sensed pressure in the sensing passage. The pressure sensor communicates with a controller which receives signals from the pressure sensor and controls the operation of other components of the apparatus.

The apparatus further includes a valve. The valve has an inlet which is fluidly connectable to a flow regulated oxygen supply. The valve further includes an outlet. The valve outlet is fluidly connectable to the delivery passage to enable the delivery of oxygen to the patient's nasal passage.

A flow rate controlling regulator is fluidly connected between the oxygen supply and the valve inlet. The flow rate controlling regulator is set to a prescribed rate of continuous flow established as providing the optimum therapeutic benefit for the patient. When the valve is in an open condition oxygen is delivered at the prescribed flow rate to the delivery passage and the patient. When the valve is in the closed condition the flow of oxygen to the patient is interrupted.

The pressure sensor senses pressure in the sensing passage which corresponds to pressure in the patient's nasal passage during the patient's breathing cycles. When the sensed pressure falls, corresponding to inhalation by the patient, the controller is operative to open the valve and deliver oxygen at the prescribed flow rate to the nasal passage of the patient for a calculated delivery period. The controller calculates the delivery period responsive to the physiological requirements of the patient, as well as the current respiration rate and respiration characteristics of the patient. The controller executes a computer program including fuzzy logic to minimize the instances where oxygen is delivered in response to negative pressure conditions that are sensed in the patient's nasal passage, but which are not the beginning of an inhalation cycle.

The oxygen conservation apparatus further includes a visual indicator which indicates each delivery of oxygen to the patient. The apparatus further includes an audio indicator, which along with the visual indicator, is controlled by the controller to indicate when the apparatus has failed to sense inhalation by the patient for a first time period which is excessive. Upon the apparatus failing to sense inhalation for a further time period, the controller is operative to open the valve to provide continuous flow.

The conserving apparatus of the preferred embodiment is battery powered. If battery power is low, the visual indicator gives a visual indication of such battery power each time oxygen is delivered.

The preferred embodiment further achieves rapid response to the controller providing a signal to open the valve when oxygen is to be delivered. This is achieved by delivery of an overdrive signal to the solenoid of the valve which causes it to change rapidly to the open condition. However, after the valve has opened, battery power is conserved through pulse width modulation of the signal to the solenoid of the valve.

In the preferred embodiment of the invention operation of the apparatus by a user is controlled through a single manually actuated switch. Movement of the switch changes the device between a conserve mode and a continuous flow mode. When the apparatus is changed to the continuous flow mode, assurance of flow is provided through a mechanical connection or linkage between the manually actuated switch and the valve. The mechanical connection ensures that the valve is in the open condition, regardless of the condition of the battery power source of the apparatus.

BEST MODES FOR CARRYING OUT INVENTION

Figure 1:
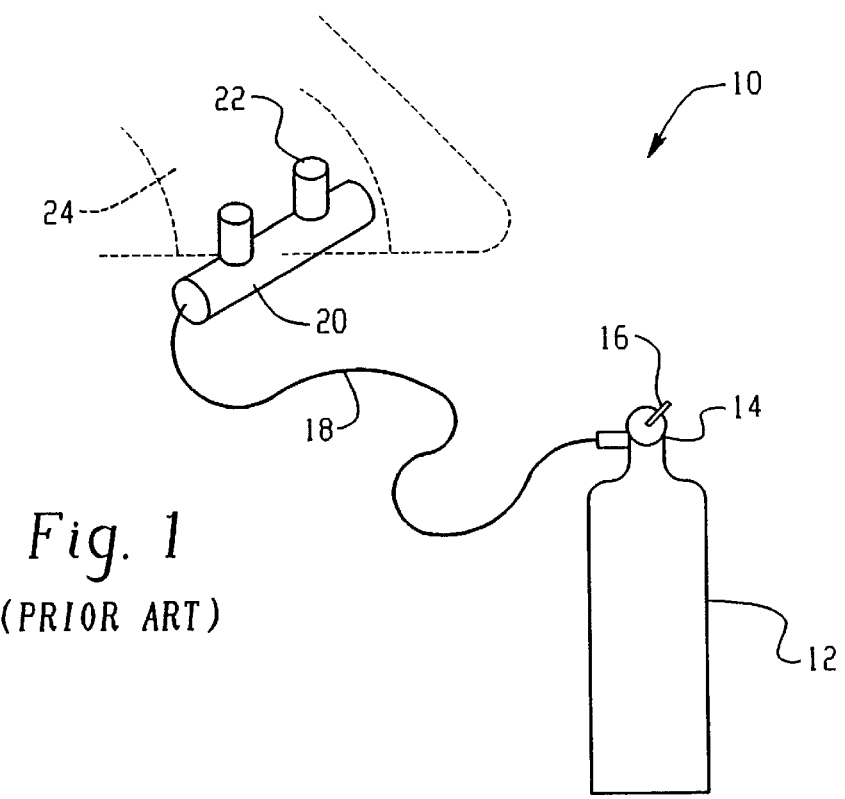
FIG. 1 is a schematic view of a conventional continuous flow supplemental oxygen supply system known in the prior art.
Figure 2:
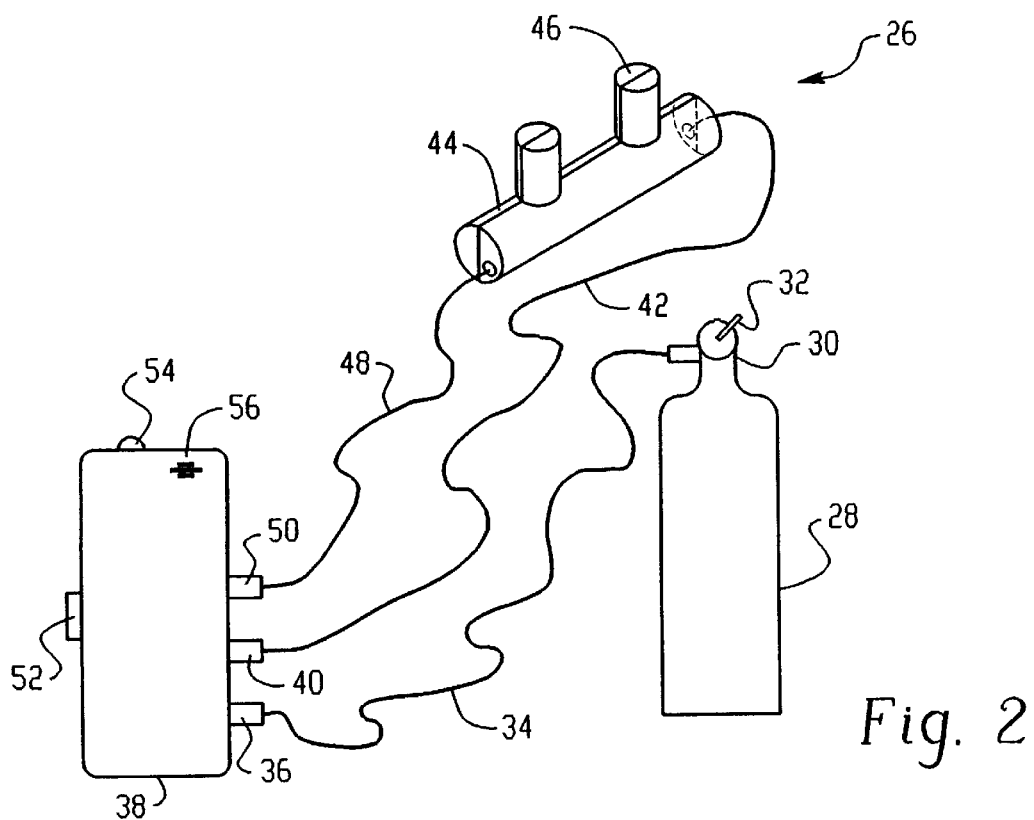
FIG. 2 is a schematic view of a supplemental oxygen supply system including the oxygen conserving apparatus of a preferred embodiment of the present invention.

Referring now to the drawings and in particular to FIG. 2, there is shown therein a system generally indicated 26 comprising an oxygen conserving apparatus of a preferred embodiment of the present invention. The system comprises an oxygen supply 28, which in the preferred embodiment of the invention is a portable oxygen supply such as a pressurized oxygen bottle. Of course in other embodiments other forms of oxygen supplies may be used, including non-portable supplies.

Oxygen supply 28 is in fluid communication with a flow rate controlling regulator 30. In the preferred form of the invention regulator 30 is a pressure compensated regulator capable of delivering up to about ten liters of oxygen per minute at about 80 psi. Examples of regulators suitable for use in the preferred form of the invention include Models XR-3000 and XA-2800 manufactured by the Western Enterprises Division of the Scott Fetzer Company Inc. Regulator 30 includes a flow setting adjustment member 32. Adjustment member 32 may be manually adjusted to provide flow from the oxygen supply 28 at a prescribed flow rate for a patient.

Oxygen is delivered from the regulator 30 through a supply line 34. Supply line 34 is connected to an inlet 36 of the conservation unit 38. Unit 38 further includes an outlet 40. Outlet 40 is in fluid communication with a delivery passage 42, which is connected to a cannula 44. Cannula 44 includes a pair of cannula passages 46 each of which is in fluid communication with a nasal passage of a patient during operation of the system.

Cannula 44 is further in communication with a sensing passage 48. Sensing passage 48 fluidly extends to a sensing port 50 on the unit 38.

In the preferred form of the invention, cannula 44 is a dual cannula wherein the sensing passage 48 and delivery passage 42 are fluidly separated throughout the cannula. Although in the described embodiment a dividing wall type cannula is shown, it should be understood that in other embodiments other types of dual cannulas, including coaxial tube types, may be used. This design enables the sensing passage and delivery passage to both be in fluid communication with the nasal passage of the patient at all times during the operation of the apparatus.

The unit 38 further includes a manually actuated switch 52. In the preferred form of the invention, manually actuated switch 52 is a switch that is manually moveable between a first switch position wherein the unit operates to conserve oxygen, and a second switch position wherein the unit provides continuous oxygen flow to the cannula. The single switch operation of the unit which is further explained, facilitates use of the present invention by persons who may be suffering from debilitating medical conditions.

The unit 38 further includes a visual indicator 54. Visual indicator 54 in the preferred form of the invention is a two color LED. The unit 38 further includes an audio indicator 56. The audio indicator in the preferred form of the invention is a piezoelectric sound emitter or "buzzer". The operation of visual and audio indicators are hereinafter explained in detail.

Figure 3:
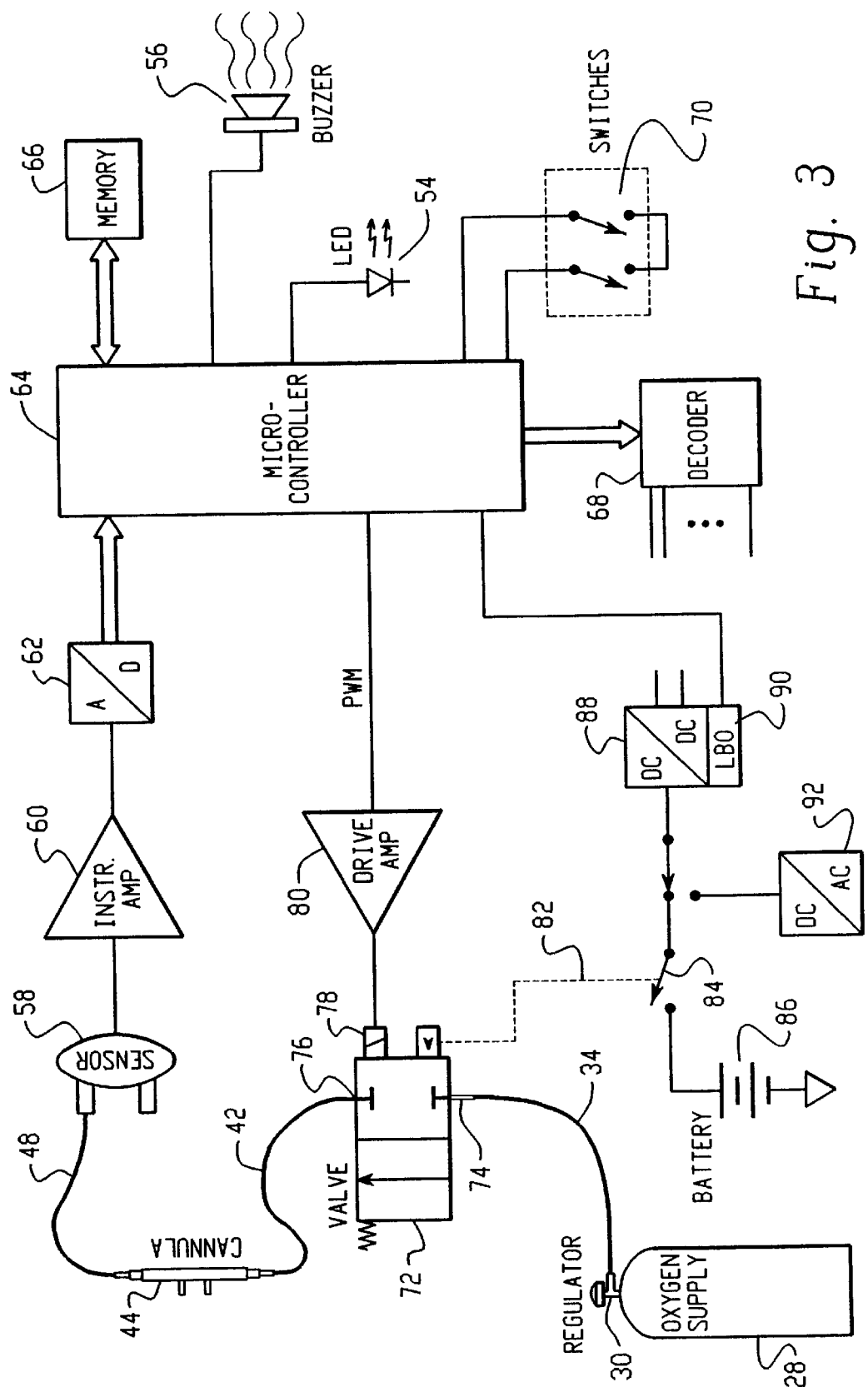
FIG. 3 is an electrical and control logic schematic of the oxygen conserving apparatus of the preferred embodiment of the present invention.

An electrical and control logic schematic of the apparatus of the present invention including the unit 38 is shown in FIG. 3. The sensing passage 48 from the cannula 44 is in connection through the sensing port 50 with a pressure sensor 58 which is housed inside the body of the unit 38. In the preferred embodiment of the present invention, the pressure sensor 58 is a semi-conductor type pressure transducer which includes a piezoelectric bridge circuit. The sensor is operative to provide an analog signal which varies linearly responsive to the sensed pressure in the sensing passage 48.

The analog signal from the pressure sensor 58 is output to an instrument amplifier 60. Instrument amplifier 60 serves to amplify the analog signals from sensor 58. In the preferred form of the invention the instrument amplifier provides a gain of about 400. In the preferred embodiment because voltage gain is high, there is some risk that external electromagnetic radiation (EMI/RFI) could induce false electrical signals. Therefore, to reduce interference a low pass filter is provided that attenuates signals with frequencies greater than 35 Hertz.

The conditioned analog pressure signals from instrument amplifier 60 are delivered to an analog to digital (A/D) converter 62. A/D converter 62 receives the analog signals and outputs corresponding digital signals. In the preferred embodiment A/D converter 62 is an eight bit successive approximation converter.

The digital pressure signals produced by the pressure signal generating apparatus comprised of the sensor, instrument amplifier and A/D converter, is delivered to a micro-controller 64. Micro-controller 64 includes a processor which executes computer programs and serves to control the operation of other components within the unit 38.

Micro-controller 64 is in operative connection with a memory 66 that stores the computer programs which are executed by the micro-controller. In the preferred embodiment of the invention, memory 66 is a firmware memory.

Micro-controller 64 is also in operative connection with a decoder 68. The decoder serves as a communications interface and is used by the micro-controller to address other semi-conductor components within the unit 38.

The micro-controller is also in operative connection with the visual indicator 54 in the preferred form of the invention. Visual indicator 54 is a bi-color light emitting diode (LED). In the preferred form of the invention, the LED is selectively controlled to flash either red or green. The micro-controller 64 is also in operative connection with the audio indicator 56.

Micro-controller 64 is also in operative connection with an input device schematically indicated 70. Input device 70 enables a variable input value to be input to the micro-controller. In the embodiment shown, the input device includes a pair of manually selectable dip switches. These dip switches are housed within the body of the unit 38, but may be accessed and manually changed by a medical technician when necessary.

The input device 70 is operative to provide an input value which is representative of a percentage of the patient's inhalation cycle that oxygen is to be delivered. In the embodiment of the invention shown, the four possible switch settings are used to set the oxygen delivery time at a value ranging from 30 to 80 percent of the patient's inhalation cycle. The particular physiological needs of the patient determine the setting that is appropriate for input device 70. It should be understood that in other embodiments of the invention, other types of input devices that are capable of receiving a variable input value, which is representative of the amount of oxygen that should be delivered to the patient, may be used.

The unit further includes a valve 72. Valve 72 includes a valve inlet 74 which is in fluid communication with the inlet 36 to the unit 38. Valve 72 also includes a valve outlet 76 which is fluidly connected to the outlet 40 of the unit and the delivery passage 42 which delivers the oxygen to the cannula 44.

In the preferred form of the invention, valve 72 is a two-condition solenoid actuated valve. In a first valve condition, flow from the oxygen supply 28 to the cannula 44 through the valve is prevented. This is represented by the schematic of the valve 72 shown in FIG. 3. In a second condition of the valve, oxygen is enabled to pass through the valve to the cannula. Valve 72 changes from the first condition to the second condition responsive to the delivery of a drive signal to a solenoid 78 of the valve 72.

The drive signal is provided to the solenoid from a drive amplifier 80. The drive amplifier is operative responsive to signals from the micro-controller 64 to provide a drive signal which is suitable for energizing the solenoid 78 and changing the valve from the first condition to the second condition in which oxygen is delivered to the cannula. The valve changes from the second condition to the first condition when the drive signal is discontinued.

In the preferred form of the invention, solenoid 78 has a power rating which is the recommended power needed to change the condition of the valve. As later discussed, in the preferred embodiment of the invention, the controller 64 and drive amplifier 80 are operative to overdrive the solenoid which causes it to open more quickly. After the valve is open, the controller is operative to pulse width modulate the overdrive voltage in a manner which is sufficient to hold the solenoid in the second condition. This reduces the amount of power required to hold the valve in the open condition.

A mechanical linkage, schematically indicated 82, is also operatively connected to valve 72. As later discussed, mechanical linkage 82 is operatively connected to manually actuated switch 52 on the unit. The mechanical linkage 82 is operative in a second switch position to mechanically cause components of the valve to be moved so the valve is in the second condition and held therein. This assures that the full prescribed flow of oxygen set at the regulator 30 flows to the patient through the cannula when the manual switch 52 is in the second switch position.

The manually actuated switch 52 is also operative to change the condition of an electrical switch 84. A battery power source, schematically indicated 86, is positioned inside the housing of unit 38. Electrical switch 84 is operative in the first position of manual switch 52 to connect battery power source 86 to the micro-controller and the other electrically operated components within the unit. In a second position of manually actuated switch 52 in which valve 72 is mechanically moved to the open condition, electrical switch 84 is operative to electrically disconnect the battery from the other components of the unit. In the preferred form of the invention, the battery power source is a pair of 1.5 volt AA size batteries.

In the closed condition of electrical switch 84 the battery power source 86 is connected to a DC to DC converter 88. The converter 88 operates to convert the battery voltage to a higher fixed voltage level. In the preferred embodiment, the DC to DC converter is operative to increase battery supply voltages of from 1.7 volts to 3.6 volts to a 5 volt level, which is optimum for the operation of the electrical components of the system.

DC to DC converter 88 is in operative connection with a low battery condition detection device 90. Low battery detection device 90 is in operative connection with the controller 64, and is operative to provide a "low battery" signal if the voltage level from the battery power source 86 to the DC to DC converter falls below a set level. As later discussed in detail, controller 64 operates responsive to a "low battery" signal from low battery detector 90 to cause the bi-color LED, which comprises the visual indicator 54, to "flash red" each time the valve 72 delivers oxygen. This red flash of the LED indicates to the patient that the battery condition is low. The controller is operative to cause the LED to "flash green" each time the valve is opened when the battery voltage is above the set level.

The unit 38 also includes therein an AC to DC converter 92. The AC to DC converter operates to disconnect the battery power source 86 from the other components of the system and supply power at a suitable DC voltage to the components of the system. Converter 92 enables a patient to operate the system from an AC power source such as 110 volt house current to prolong battery life, as well as during battery replacement.

During operation of the apparatus of the present invention, each passage 46 of cannula 44 is extended into a nasal passage of a patient. As the patient breathes, pressure sensor 58 senses the variations in pressure in the sensing passage 48 which are caused by the patient's respiration. Each time the patient inhales a negative pressure is sensed by the pressure sensor. Likewise, each time the patient exhales, a positive pressure is sensed by the pressure sensor. These variations in pressure occur repeatedly during each respiration cycle.

Respiration cycles may vary dramatically in rate and character depending on the condition and activity level of the patient. There is also generally a dwell or rest time between respiration cycles during which the patient is neither inhaling or exhaling. In addition, due to irregular breathing, coughing, talking, and other activities, a patient may exhibit respiration cycles which include two or more distinct inhalation periods before an exhalation cycle, or vice versa. These many possible variations of respiration cycles present challenges in attempting to provide supplemental oxygen to a patient at a point in their respiration cycle which provides optimum therapeutic benefit.

Figure 4:
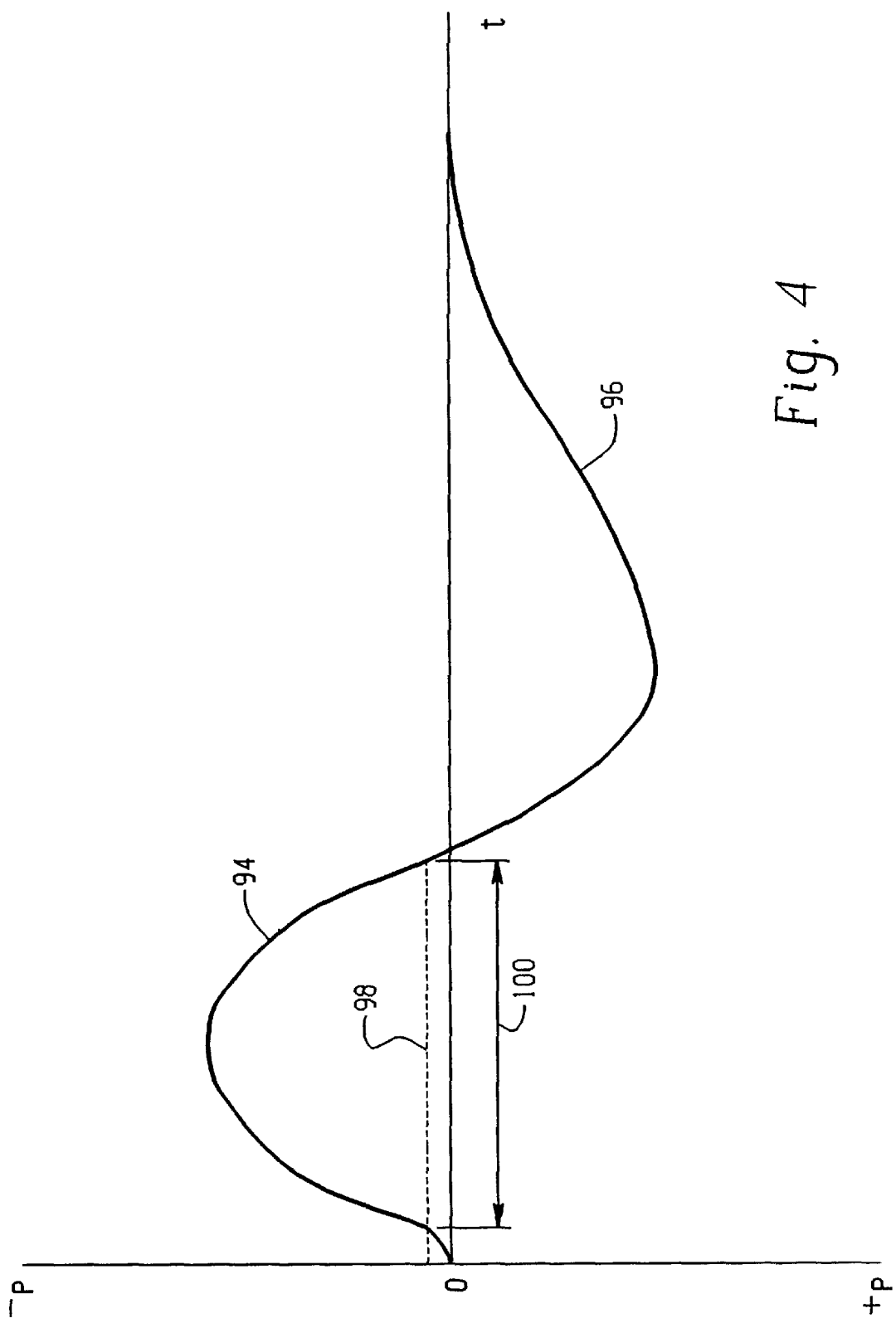
FIG. 4 is a graph representing the variation in pressure in a nasal passage of a patient as a function of time during a respiration cycle.

Variations in pressure sensed by the pressure sensor 58 as a function of time during a sample respiration cycle is graphically shown in FIG. 4. As the patient inhales, a negative pressure shown in FIG. 4 as above the zero line is generated. This period of negative pressure 94 represents an inhalation cycle of the patient. When the patient stops inhaling, the sensed pressure falls to zero and then rises to a positive pressure during an exhalation cycle 96. As the patient finishes exhaling, the positive pressure moves back towards the zero pressure line and generally remains for a dwell time until the patient begins another inhalation cycle.

In the preferred form of the present invention, the apparatus is operative to sense when the sensed pressure reaches and drops below a threshold level which is indicated 98 in FIG. 4. In accordance with the invention, a quantity indicative of the time that the sensed pressure has reached and is below the threshold level, indicated by Arrow 100 in FIG. 4, is measured. In the preferred form of the invention the threshold level is set at about negative 0.4 centimeters of water. The threshold level is set at about this value because it is sufficiently disposed from the zero pressure level to be indicative of an inhalation cycle occurring, while still far enough away from the zero pressure level that the unit is not overly sensitive to changes in pressure due to causes other than inhalation.

In the preferred form of the invention, the micro-controller 64 is programmed to generate internally a digital pressure signal of "1" when sensed pressure is at or below the threshold. When the sensed pressure is above the threshold, the controller 64 produces an internal pressure signal of "0".

Figure 5:
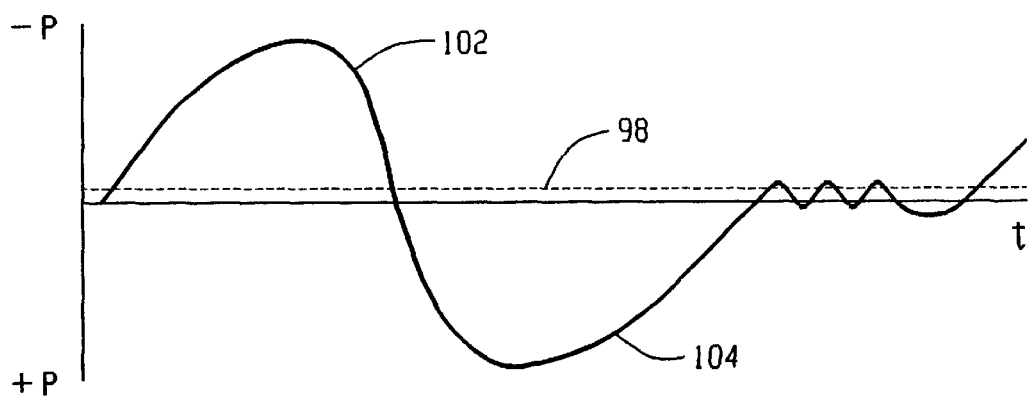
FIG. 5 is a graph representing the variation in pressure in a nasal passage of a patient as a function of time during a further respiration cycle.
Figure 6:
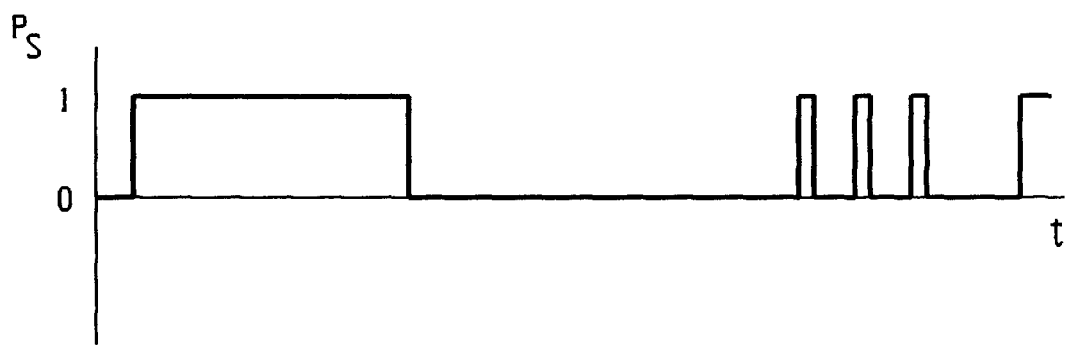
FIG. 6 is a graph showing variation in a pressure signal within the conserving apparatus corresponding to the respiration cycle shown in FIG. 5.

The relationship between the pressure signals produced by the controller 64 during a patient's respiration cycle is graphically represented in FIGS. 5 and 6. FIG. 5 shows variations in pressure as a function of time during one respiration cycle. During an inhalation cycle 102 the patient's nasal pressure drops below threshold level 98. During the time that the sensed pressure is at or below the threshold level, the controller produces a continuous signal. As the patient's nasal pressure rises above the threshold, and during an exhalation cycle 104, a "0" signal is produced. As later discussed in detail, the crossing of the threshold level by the sensed pressure is used by the micro-controller to initiate the opening of valve 72 and the delivery of oxygen to the patient. In addition, the controller 64 uses a quantity indicative of the time that the sensed pressure is at or below the threshold during an immediately preceding inhalation cycle to calculate a time period that oxygen will be delivered to the patient during the next inhalation cycle.

As shown to the right in FIG. 5, the breathing patterns of a patient may cause pressure fluctuations which cause the sensed pressure to cross the threshold level 98 at times which do not represent the beginning of an inhalation cycle. Such unpredictable transient fluctuations have the potential for causing a supplemental oxygen delivery device to deliver oxygen at times which will provide no therapeutic benefit to the patient.

In the preferred embodiment of the invention, this problem is reduced through the use of a fuzzy logic program which operates in controller 64. The fuzzy logic program determines whether it is appropriate to deliver oxygen to the patient when the sensed pressure falls and reaches the threshold level in response to a timed relationship among pressure signals. In executing the fuzzy logic, the controller 64 calculates a function of a quantity which corresponds to the elapsed time since the sensed pressure last crossed the threshold level. Similarly, the fuzzy logic also considers and calculates a function of a quantity which corresponds to the elapsed time since the sensed pressure has been above the threshold level. Finally, in the preferred embodiment, the controller 64 also determines whether oxygen should be delivered based on a function of the elapsed time since the valve 72 has been open.

In the preferred embodiment the fuzzy logic program executed by controller 68 works on the principle of using a plurality of counters to make a decision as to whether currently existing conditions, when the sensed pressure reaches the threshold level, is "more like" the beginning of an inhalation cycle or is "more like" a fluctuation during an exhalation cycle or during a dwell or rest period. The controller senses and counts the pressure signals at the uniform operating rate of the processor in the controller 64 as either part of inhalation or as part of exhalation. If the counts representative of elapsed time have reached levels which suggest that the particular occurrence of sensed pressure crossing the threshold appears to be the beginning of an inhalation cycle and not a short transient fluctuation in pressure, the controller is operative to deliver oxygen to the patient for a time period calculated in accordance with its programming.

Figure 7:
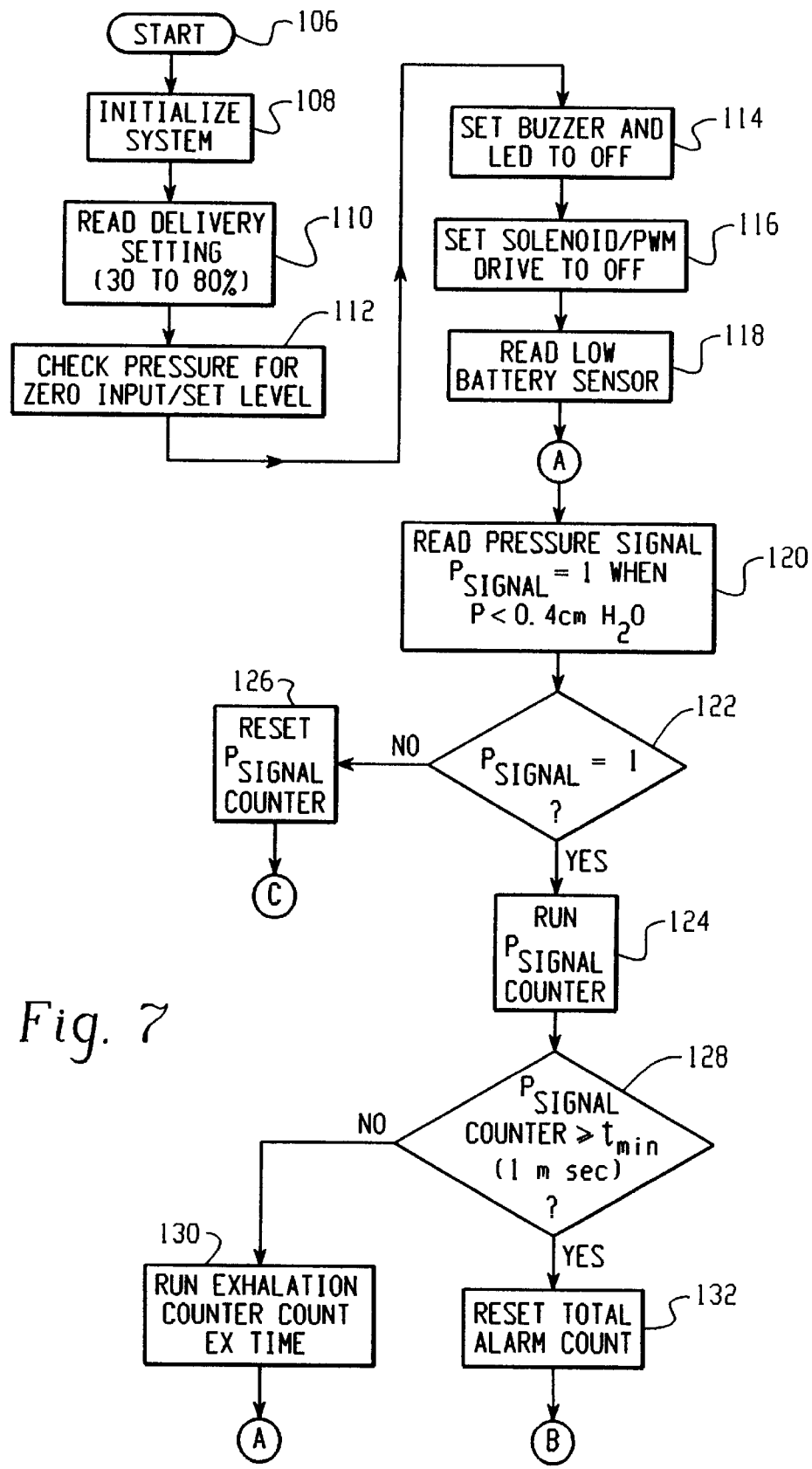
FIGS. 7, 8 and 9 are a flow chart schematically representing steps in a computer program executed by a controller of the oxygen conserving apparatus of the present invention.
Figure 8:
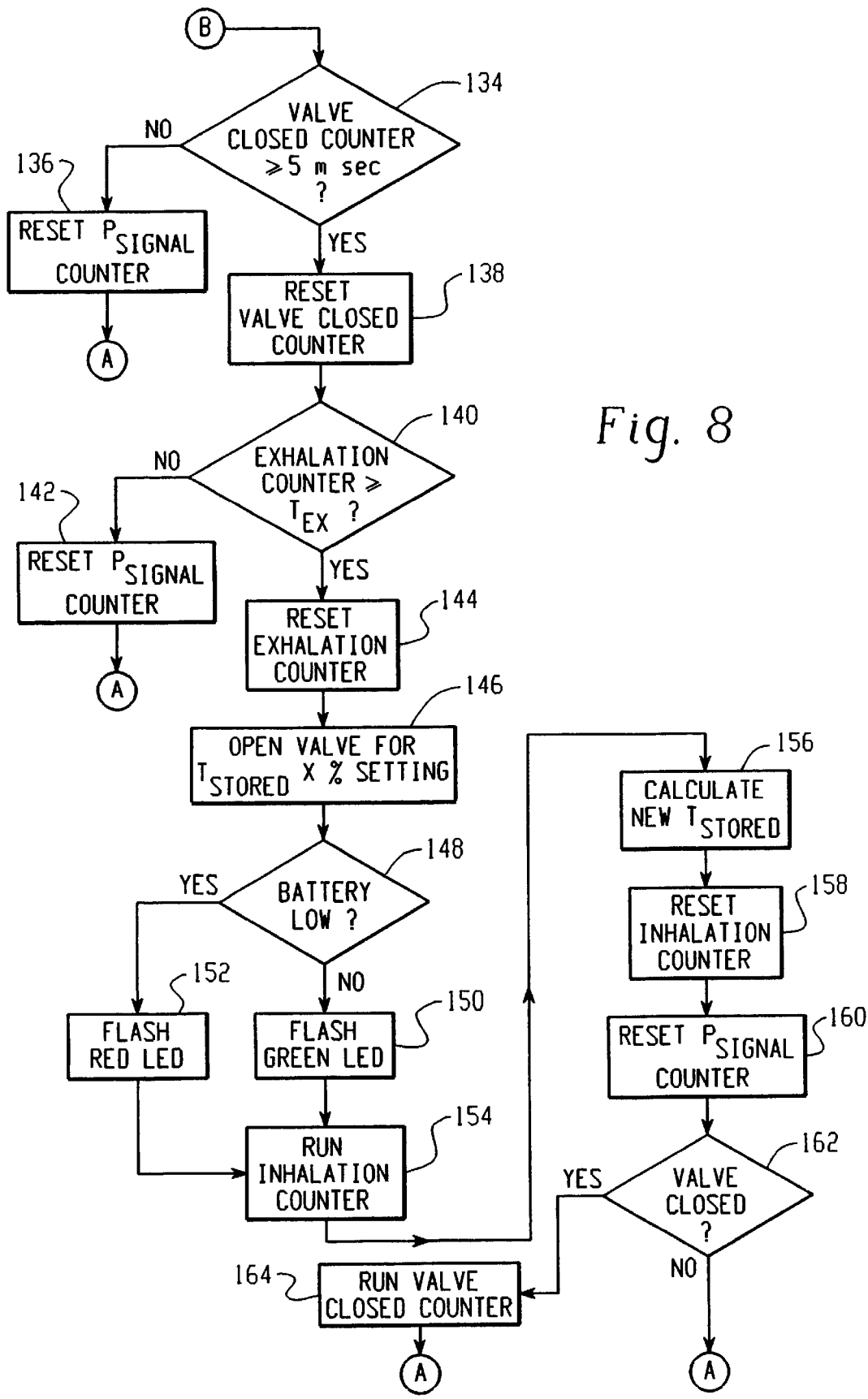
Figure 9:
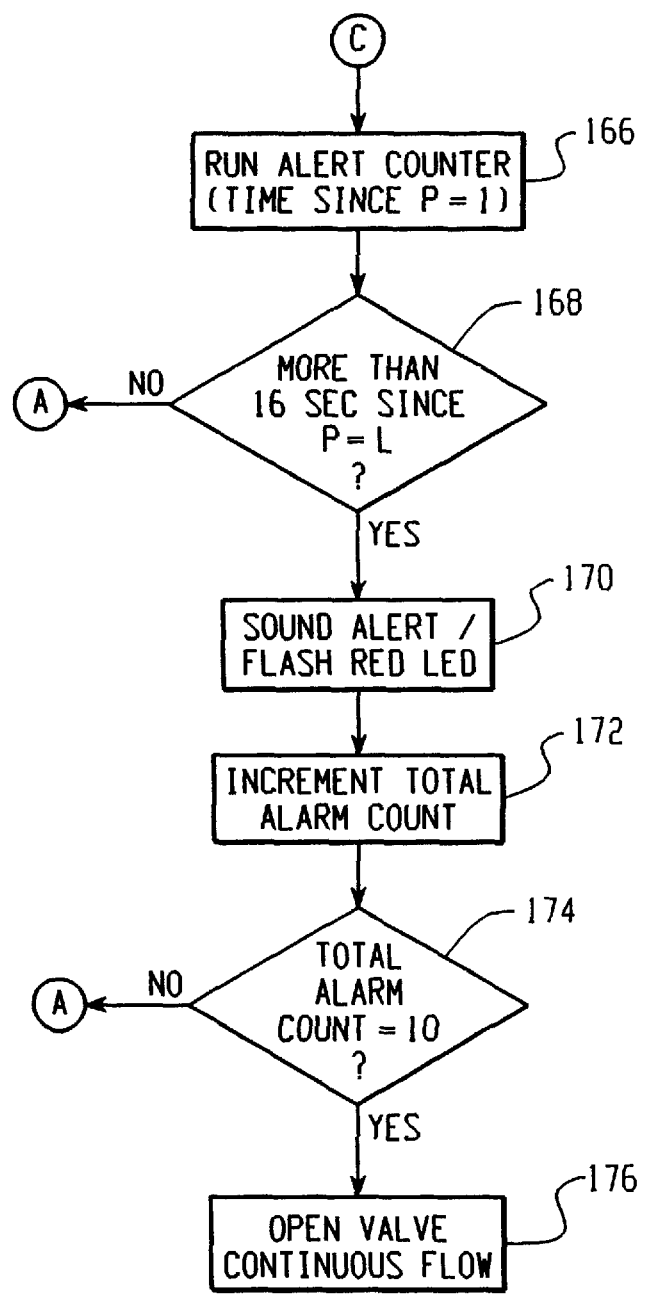

The operation of the fuzzy logic program executed by the controller 64 is shown schematically in FIGS. 7–9. From a program start 106 the controller first operates to initialize the system in a step 108. In the initialization step the controller establishes the appropriate initial values in the counters, sets parameters and the like.

After the system is initialized the controller is operative in a step 110 to read the input value from the input device 70. As previously discussed, in this preferred embodiment the input device is manually changeable between four values which span a range from 30% to 80% of a time quantity calculated by the controller 64. The setting of the input device is based on the physiological requirements of the patient which are predetermined through medical testing of the patient at various activity levels. The input device is set based on the patient's tested ability to absorb oxygen so as to maintain the desired $SaO_2$ level.

The controller next executes a step 112 in which it checks the pressure signal from the pressure sensor and pressure signal generating apparatus. The controller checks for a zero pressure input based on a zero pressure reference value stored in memory. The controller also checks for any signal drift and "re-zeros" its zero position. Thereafter the controller is operative to set the threshold level based on the sensed zero pressure level. As previously discussed, in the preferred form of the invention the threshold level is set at about minus 0.4 centimeters of water. Of course in other embodiments other threshold levels may be used.

The controller next sets the visual indicator 54 which includes the bi-color LED, and the audio indicator 56 which includes the piezoelectric buzzer, to the "off" condition at a step 114. Thereafter at a step 116 the controller shuts off signals to the drive amplifier 80 which drives the solenoid of valve 72 and sets the pulse width modulation control for the signal to "off".

The controller then reads the signal from the low battery detector 90 at a step 118. Although not shown in the flow chart in FIG. 7, if the battery is found to have a low voltage in step 118, the visual and audio indicators may be actuated to indicate to the patient that the battery needs replacement. Alternatively other indicators of this condition may be provided. In the embodiment shown the low battery condition is indicated through the LED flashing red each time the valve 72 is opened as hereinafter discussed.

The controller 64 is operative to generate internally a pressure signal of "1" when the sensed pressure at the senor 58 is at or below the threshold level. The controller is also operative to provide an internal pressure signal of "0" when the sensed pressure is above the threshold level. At a step 120 the controller reads the pressure signal. At a decision step 122 a decision is made as to whether the pressure signal indicates that sensed pressure has reached or is below the threshold level. If the pressure is below the threshold the pressure signal counter is run at a step 124. Alternatively, if the pressure signal does not indicate that sensed pressure is not at the threshold at step 122, the pressure signal counter is reset at a step 126. From step 126 the controller also executes an alert and fail safe routine which will be later discussed.

If the pressure signal indicates that sensed pressure is at or below the threshold level, "counts" are accrued in the pressure signal counter at step 124 during each cycle of the microprocessor of the controller 64. At a step 128 a decision is made as to whether the number of counts in the pressure signal counting step has exceeded a number which corresponds to a set minimum. In this case the minimum corresponds to 1 millisecond. If so, this is indicative that the signal from the pressure detector is a bona fide indication of a pressure below the threshold, and is not due to interference of other transient signal fluctuation. If the pressure signal count is not beyond the minimum, the time is counted to an exhalation counter at a step 130.

If the pressure signal is found to be above the minimum time at step 128 the controller resets an alarm count at a step 132 which relates to the alert and fail safe routine which is later discussed.

If the pressure is at or below the threshold for more than the minimum period at step 128, the controller then proceeds as shown in FIG. 8 to determine whether valve 72 has been closed for more than a minimum period. This is done at a step 134. In step 134 it is determined whether the valve has been in the closed position for a period which corresponds to at least 5 milliseconds. If the valve has not been closed for at least this long the pressure signal counter is reset at a step 136.

If the valve has been closed for more than the minimum period in step 134, the valve closed counter is reset at a step 138 and the controller next proceeds to a step 140. In step 140 a decision is made as to whether the counts which have accrued in the exhalation counter have exceeded a set minimum. If so, this is indicative that a genuine period of exhalation has occurred and that the patient is now ready to inhale. The determination that a bona fide exhalation cycle has been completed causes the controller to deliver oxygen to the patient through the cannula when the pressure again falls to the threshold level in a manner later discussed. If however the exhalation counter is currently at a level which is below the set minimum, this indicates that transient pressure variations are occurring and there has not been sufficient exhalation to represent an exhalation cycle. This condition causes the pressure signal counter to be reset at a step 142.

If it is determined at step 140 that the exhalation counter is holding a count which is indicative that the patient has been exhaling for a sufficient period that an exhalation cycle has occurred, the exhalation counter is next reset at a step 144. In response to this condition and the pressure remaining at or below the threshold level, the controller is also operative to output a signal to the drive amplifier 80 to open valve 72 at a step 146.

In step 146 the controller is operative to open valve 72 for a period of time that is a function of both a time quantity and an input value set through the input device, which input value is representative of a percentage between 30% and 80%. Thus, if the input device has an input value of 30%, the duration that valve 72 will be open in step 146 is 30% multiplied by a calculated time quantity. The time quantity is calculated in a manner hereinafter discussed and varies in accordance with the respiration rate and the character of the inhalation cycles which the patient is currently experiencing.

Figure 10:
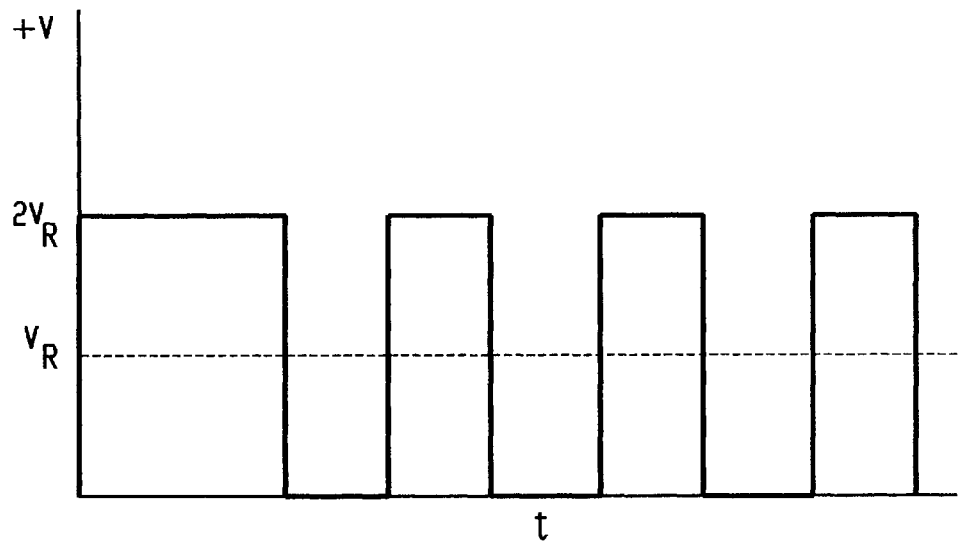
FIG. 10 is a graphical representation of voltage as a function of time for a power signal used to open a valve in the present invention and to maintain the valve in the open condition.

In opening the valve at step 146 the controller sends a signal to the drive amplifier 80 which causes a power signal to be transmitted to the solenoid 78 of valve 72. This power signal is in the form of an overdrive signal which is at a voltage that produces twice the rated power of the solenoid. As shown in the graph in FIG. 10, the overdrive signal is initially delivered continuously for a period of time sufficient to cause valve 72 to open. In the preferred form of the invention the rated voltage ($V_R$) is exceeded to the extent that the overdrive signal is twice the rated voltage of the solenoid ($2V_R$), and the overdrive signal is initially delivered continuously for 50 milliseconds to open the valve.

After the valve has been opened by the initial overdrive signal, the controller operates to pulse width modulate the drive signal. This pulse width modulated overdrive signal has a duty cycle sufficient to maintain the valve in the open condition. However the resultant reduction in power required to maintain the valve in the open condition extends battery life dramatically. In the preferred embodiment of the invention the pulse width modulation has a 50—50 duty cycle and a frequency of 2 Kilohertz.

At a next step 148 a decision is made as to whether the low battery detector 90 is indicating that the battery power source 86 is low. If the battery is not low, a green flash is given by the visual indicator 54 which includes the bi-color LED. This is done at a step 150. If the battery is low however, the controller operates to flash the bi-color LED red at a step 152. The flashing of the visual indicator each time the valve is opened provides an indication to the patient that the device is working properly. The variation in the color of the indicator tells the patient when it is time to replace the batteries in the unit or to connect the converter 92 to an AC power source. This simple yet effective indication provides patient assurance that the unit is working properly.

At a step 154 the controller is operative to run an inhalation counter. This inhalation counter provides a quantity which is indicative of a time that the sensed pressure has been continuously at or below the threshold level and which time has not been discarded by the logic of the program as interference or a short transient pressure fluctuation. The time period which corresponds to the counts accrued in the inhalation counter is then used at a step 154 to calculate a new stored time quantity at a step 156. The new stored time quantity will be used in the next inhalation cycle as part of the calculation by the controller that determines the duration that oxygen will be delivered to the patient at step 146.

In the preferred form of the invention, the time quantity is calculated as a function of a quantity representative of the time in the most recent inhalation cycle that the sensed pressure was at or below the threshold level, as well as a stored value. In the preferred form of the invention the calculation at step 156 gives greater weight to the duration of the most recent inhalation cycle of the patient in determining the new time quantity to be stored.

The formula for calculating the new time quantity in the preferred embodiment of the invention is the following formula:

$$T_{(N+1)} = \frac{F(P_t) + T_N}{(F+1)}$$

wherein:

$T_{(N+1)}$ is the new time quantity to be stored for use in calculating the duration of oxygen delivery in the next inhalation cycle F corresponds to a time weighing factor ($P_t$) corresponds to the quantity determined in step 154 in the inhalation counter which represents a time that the sensed pressure was at or below the threshold level $T_N$ is the time quantity calculated for the immediately proceeding inhalation cycle In the preferred form of the invention the time weighing factor is set at 2. In this way a new time quantity is calculated in which the duration of the most recent inhalation cycle is weighted twice as heavily compared to the previously stored value in determining the time period that oxygen will be delivered to a patient the next time the patient inhales.

Of course when the system is first started there is no prior respiration cycle from which a time quantity can be calculated. Therefore during the initialization step the controller is operative to set the first time quantity to a value that corresponds to about 1.6 seconds. This corresponds to approximately a 15 breaths per minute breathing rate. However once the apparatus begins sensing the inhalation cycles of the patient, the time quantity rapidly adjusts to the particular respiration rate and inhalation cycles of the patient.

The ability of the apparatus of the present invention to adjust the duration of the time quantity which affects the duration that oxygen is delivered to the patient is a fundamental aspect of the present invention. This feature enables the patient to receive more oxygen automatically in accordance with changes in his respiration rate and duration of inhalation cycles. This prevents the patient from becoming desaturated in his $SaO_2$ level. The invention has been found to very closely approximate the therapeutic benefits in terms of maintaining $SaO_2$ level achieved with continuous oxygen flow at a prescribed rate. The fuzzy logic employed by the present invention also achieves this result while increasing the probability that oxygen is delivered during the respiration cycle at a time when it provides optimum therapeutic benefit.

After calculating a new time quantity for use in determining the duration of oxygen delivery in the next inhalation cycle, the controller operates to reset the inhalation counter at a step 158. The controller then operates to reset the pressure signal counter at a step 160.

At a step 162 a decision is made as to whether the valve has closed. Generally as the period of inhalation will be greater than the time period that the valve is open, the valve will be closed at this step. If so, the valve closed counter is run at a step 164. As previously discussed in connection with step 134, this counter is used as part of the fuzzy logic which increases the probability that the valve is only opened during actual patient inhalation cycles.

The preferred embodiment of the present invention also includes an alerting and fail safe routine. These features are operative to alert the patient that the apparatus is not sensing the patient's inhalation. This may result due to the cannula becoming displaced from the patient's nasal passages. It could also result due to a blockage in the cannula, a kink in the tubing leading to the sensing passage or from other malfunctions. If such condition is detected, the preferred embodiment of the present invention alerts the patient so that the patient may take steps to adjust the cannula and again place the unit in proper operating condition. In accordance with the invention however, if after a period of time the unit is not sensing inhalation by the patient, then the controller operates to put the unit in a fail safe mode wherein the valve 72 is opened and oxygen is delivered continuously to the cannula.

The alert and fail safe routine executed by the controller is schematically represented by the flow chart in FIG. 9. From the step 126 in FIG. 7 wherein the pressure signal has not been found to be at or below the threshold, a step 166 is executed by the controller. In step 166 an alert counter is run which measures the quantity of counts indicative of the time since the sensed pressure from the cannnula has been at the threshold level. At a step 168 a determination is made as to whether more than a set elapsed time has occurred since nasal pressure was sensed at the threshold. In the embodiment of the invention shown this elapsed time is set at 16 seconds.

It should be understood that the elapsed time period without sensing pressure at or below the threshold generally also corresponds to at least an equal time period having elapsed without valve 72 having opened to deliver oxygen to the patient. It should be appreciated while in the embodiment of the invention shown a time since negative pressure at the threshold is used as the measured quantity in step 168, in other embodiments the time since the valve was last open and could alternatively be measured for purposes of determining when to alert a patient.

At step 168 if more than the said elapsed time has not occurred since a pressure at or below the threshold level was sensed, the system continues. However if such an elapsed time has occurred the controller executes a step 170. In step 170 the controller is operative to operate the visual and audio indicators 54 and 56 for a period of time intended to get the patient's attention. In a preferred embodiment of the invention the controller is operative in response to the execution of step 170 to flash the LED indicator on red and to sound the audio indicator continuously for 5 seconds. This is generally sufficient to alert the patient of a problem and enables them to adjust the cannula or to make other appropriate adjustment to the system.

The controller next executes a step 172. At step 172 an alarm count is incremented by one. This count is operative to provide the number of times that the time period in step 168 has sequentially occurred without the device sensing the inhalation by the patient. Of course as previously discussed in connection with step 132, if the patient makes appropriate adjustments or begins breathing such that inhalation by the patient is sensed, the alarm count is reset to zero.

If the patient is not sensed as inhaling by the time the alarm count in step 172 reaches a set level, the controller is operative to take action and cause the unit to go into a fail safe mode in which oxygen is delivered continuously to the patient. At a step 174 the current count in the counter that was incremented at step 172, is checked to see if it has reached a set level. In the embodiment shown the count is set at 10 which corresponds to 160 seconds. If the time period has not been reached, the steps are repeated until the patient is sensed as inhaling.

If however the set level in step 174 is reached, the controller is operative to execute a step 176 which transmits a signal to drive amplifier 80 to open the valve and to maintain it in a continuous flow condition until the system senses patient inhalation or is reset. In addition it may be desirable in some embodiments as part of step 176 to have the controller flash the LED and/or to sound the audio indicator continuously to get the patient's attention. This can alternatively be done on a periodic basis, such as at 16 second intervals to conserve battery power.

This feature is desirable from the standpoint that the fail safe mode will supply oxygen to the patient if a malfunction has caused the unit to no longer to be able to sense the patient's inhalation cycles. However, if the patient has disconnected the cannula and set the unit aside, the visual and audio signals will remind the patient that oxygen is being wasted and the flow from the regulator 30 on the oxygen supply 28 should be turned off to conserve oxygen.

A fundamental aspect of a preferred embodiment of the invention is that it is easy to operate. The patient has only the single manually actuated switch 52 to manipulate to control the unit. It should be remembered that the input device 70 is preferably set by a medical technician or other qualified person to the physiological requirements of the patient. The switches which comprise the input device are generally not modified by the patient in the preferred embodiment, as the input device is housed within the body of the unit 38.

It should be noted that in other embodiments however, provisions may be made for the controller 68 to receive dynamically variable input values rather than the set values provided by input device 70. Such dynamically variable input values may be obtained from other sensors which measure the patient's physiological factors which are used by computer programs operating within the controller to modify the duration of oxygen delivery. Such suitable sensors for determining physiological conditions may include a heart rate monitor, oximeter, breath flow rate sensor and/or combinations of these or other sensor signals which are found to be predictive of the patient's need for more or less supplemental oxygen.

A further fundamental advantage of the preferred embodiment of the invention is that patients who are accustomed to using conventional continuous oxygen therapy should not accidentally place the unit in a condition which prevents the flow of supplemental oxygen. Rather the unit may be adjusted by the patient through the manually actuated switch 52 only between a condition where the device is operative in the conserve mode or a condition in which oxygen passes therethrough continuously at the prescribed rate.

Figures 11, 12:
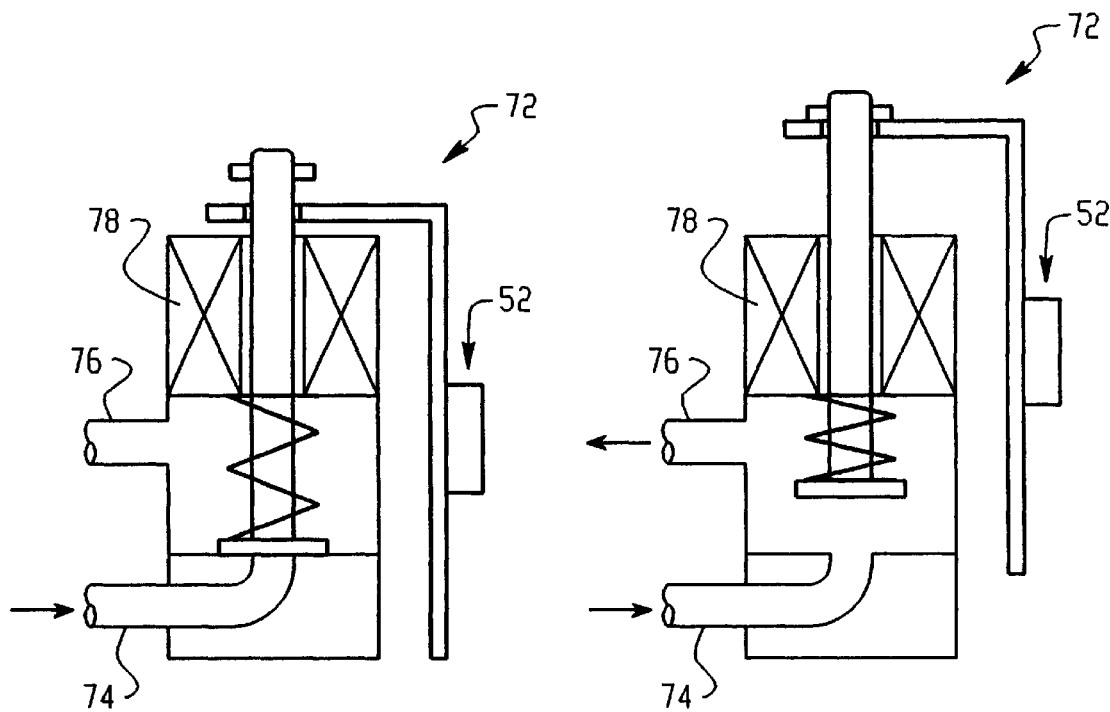
FIG. 11 is a schematic view of the valve of the present invention and a manually actuated switch in a first switch position, wherein said valve is enabled to open and close.
FIG. 12 is a schematic view of the valve shown in FIG. 11 wherein the manually actuated switch is in a second position wherein said valve is mechanically held in an open condition.

As graphically demonstrated in FIGS. 11 and 12, in a first position of switch 52 shown in FIG. 11, valve 72 is enabled to open and close responsive to the delivery of electrical signals to solenoid 78. However, as shown in FIG. 12 when switch 52 is moved to the second switch position, a mechanical linkage is operative to mechanically move the valve components so that continuous flow is provided. In addition as previously discussed in connection with electrical switch 84, moving switch 52 to the second switch position shown in FIG. 12 disconnects battery power to extend battery life.

The preferred embodiment of the present invention is operative to provide oxygen to the patient in a manner that is dynamically tailored to the patient's physiological needs. The device closely approximates the beneficial effects of continuous oxygen therapy while conserving the oxygen supply and extending the patient's ability to utilize a single portable oxygen source or a source having a smaller oxygen generating capacity.

A further advantage of the present invention is that a person who is accustomed to conventional continuous flow oxygen therapy may readily adapt to using the apparatus of the present invention. It simply operates in either the continuous or conserve modes and is controlled through a single switch. It is easy to use by any patient who can manually manipulate the switch. In addition, the unit enables a patient to continue to use their existing oxygen supply type and regulator which minimizes the cost to the patient. Further, unlike devices which deliver high pressure pulses to the nasal passages of the patient, the apparatus of the preferred embodiment of the present invention is much more comfortable for the patient to use for extended periods of time.

Thus the new supplemental oxygen delivery apparatus and method of the present invention achieves the above stated objectives, eliminates difficulties encountered in the use of prior devices and systems, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations given herein are by way of examples and the invention is not limited to the exact details shown or described.

Further in the following claims any feature described as a means for performing a function shall be construed as encompassing any means capable of performing the recited function and shall not be deemed limited to the particular means shown herein performing the function or mere equivalents.

Having described the features, discoveries and principles of the invention, the manner in which it is constructed, operated and utilized, and the advantages and useful results attained; the new and useful structures, devices, elements, arrangements, parts, combinations, systems, methods, equipment, operations and relationships are set forth in the appended claims.

I claim:

1. An apparatus for conserving oxygen being delivered from an oxygen supply to a patient comprising:

a sensing passage fluidly connectable to a nasal passage of a patient, and a delivery passage separated from said sensing passage, wherein said delivery passage is fluidly connectable to a patient's nasal passage;

a valve, wherein said valve includes a valve inlet, wherein said valve inlet is fluidly connectable to an oxygen supply, and wherein said valve further includes a valve outlet, wherein said valve outlet is fluidly connectable to said delivery passage, and wherein said valve is selectively changeable between a first valve condition wherein said valve inlet and valve outlet are not in fluid communication, and a second valve condition wherein said valve inlet and valve outlet are in fluid communication;

a pressure sensor, wherein said pressure sensor is in fluid communication with said sensing passage, and wherein said sensor is operative to a sense a sensed pressure in said sensing passage;

a controller in operative connection with said pressure sensor and said valve, wherein said controller is operative to cause said valve to change from the first condition to the second condition responsive to said senses pressure reaching a threshold level; and a manually actuated switch, wherein said switch is manually movable between a first switch position and a second switch position, wherein said manual switch is in operative connection with said valve, and wherein in the first switch position said valve is enabled to change responsive to said controller between said first and second valve conditions, and wherein in the second switch position said valve is continuously in the second condition.

2. The apparatus according to claim 1 and further comprising a pressure signal generating apparatus, wherein said pressure signal generating apparatus generates pressure signals responsive to said sensed pressure, and wherein said controller is operative to execute a program, and wherein said program is operative to cause said controller to change said valve from said first condition to said second condition responsive to said pressure signals.

3. The apparatus according to claim 2 wherein said program is operative to prevent said change in valve condition when said sensed pressure reaches said threshold level, responsive to a timed relationship among said pressure signals.

4. The apparatus according to claim 3 wherein said timed relationship is a function of a quantity corresponding to an elapsed time since said sensed pressure last reached said threshold level.

5. The apparatus according to claim 3 wherein said timed relationship is a function of a quantity corresponding to an elapsed time that said pressure signal has been above said threshold level.

6. The apparatus according to claim 2 wherein said program includes fuzzy logic.

7. The apparatus according to claim 1 wherein said controller is operative to maintain said valve in the second condition for a variable delivery period each time said valve changes from said first condition to said second condition.

8. The apparatus according to claim 7 wherein said delivery period in a current inhalation cycle is calculated by said controller as a function of a quantity corresponding to a prior time interval, wherein said prior time interval corresponds to a time in said immediately proceeding inhalation cycle that said sensed pressure was at least as low as said threshold level.

9. The apparatus according to claim 8 wherein in calculating said function said quantity corresponding to said prior time interval is weighed more heavily than other time based parameters which comprise said function.

10. The apparatus according to claim 7 and further comprising an input device, wherein said input device accepts a variable input value, and wherein said controller calculates said delivery period as a function of said input value.

11. The apparatus according to claim 10 wherein said input device is manually changeable, and wherein said input value is variable responsive to manual changes to said input device.

12. The apparatus according to claim 11 wherein said input value corresponds to a percentage set through said input device, whereby said percentage corresponds to the portion of each inhalation cycle during which oxygen is delivered to such a patient.

13. The apparatus according to claim 10 wherein said delivery period for a current inhalation cycle of a patient is calculated by said controller as a first function which includes a product of said variable input value and a time quantity, wherein said time quantity is calculated as a second function of a prior time value corresponding to a time said sensed pressure was at least as low as said threshold level during an immediately proceeding inhalation cycle.

14. The apparatus according to claim 13 wherein said time quantity is calculated generally in accordance with the following mathematical relation:

$$T_{(N+1)} = \frac{F(P_t) + T_N}{(F + 1)}$$

wherein:

$T_{(N+1)}$ corresponds to a time quantity for a next inhalation cycle

F corresponds to a time weighing factor $(P_t)$ corresponds to a time in a current inhalation cycle wherein sensed pressure is at least as low as the threshold level; and $T_N$ is a time quantity calculated in accordance with the formula in the immediately proceeding inhalation cycle.

15. The apparatus according to claim 14 wherein F is generally about 2.

16. The apparatus according to claim 1 and further comprising a flow rate controlling regulator positioned fluidly intermediate of said oxygen supply and said valve inlet, and wherein said flow rate controlling regulator provides oxygen flow at a prescribed rate for said patient, and wherein in the second condition of said valve oxygen flows from said valve outlet at said prescribed rate.

17. The apparatus according to claim 16 wherein said regulator is a pressure compensated flow regulator.

18. The apparatus according to claim 16 wherein said oxygen supply includes a bottle containing oxygen under pressure, and wherein said regulator is in supported connection with said bottle, and wherein said regulator further comprises a flow setting adjustment member, wherein adjustment of said member is operative to adjust said prescribed flow rate.

19. The apparatus according to claim 1 and further comprising a visual indicator in operative connection with said controller, and wherein said visual indicator is operative to provide a visual indication each time the valve changes to the second condition.

20. The apparatus according to claim 19 and further comprising a battery power source in operative connection with the visual indicator, and further comprising a low battery condition detection device in operative connection with the battery power source and the visual indicator, wherein said detection device is operative to detect a low battery condition, and wherein said visual indicator gives a first visual indication each time the valve changes to the second condition when the low battery condition is not detected, and a second visual indication when said low battery condition is detected.

21. The apparatus according to claim 20 wherein said first visual indication includes a display which includes a different color from said second visual indication.

22. The apparatus according to claim 1 wherein said manually actuated switch is in operative mechanical connection with said valve, and wherein in the second switch position said valve is mechanically maintained in the second valve condition.

23. The apparatus according to claim 22 and further comprising an electrical switch in operative connection with said manually actuated switch, and wherein said electrical switch is in operative connection with said controller, and wherein in said first position of said manual switch said controller is enabled to change said condition of said valve responsive to electrical power supplied through said electrical switch.

24. The apparatus according to claim 23 and further comprising a battery power source, wherein in said first manual switch position said battery power source is in operative connection with said valve through said electrical switch, and wherein in the second manual switch position said battery power source is operatively disconnected from said valve.

25. The apparatus according to claim 1 wherein said controller is operative responsive to an occurrence to maintain said valve continuously in the second condition.

26. The apparatus according to claim 25 wherein said occurrence corresponds to said valve not being in the second valve condition for a time.

27. The apparatus according to claim 25 wherein said occurrence corresponds to said sensed pressure not being at least as low as said threshold level for a time.

28. The apparatus according to claim 1 and further comprising an indicator in operative connection with said controller, and wherein said controller is operative to actuate said indicator to give an indication responsive to a first occurrence, wherein said occurrence corresponds to said sensed pressure not reaching said threshold level for a first time period.

29. The apparatus according to claim 28 wherein said occurrence further corresponds to said valve not having been in the second condition for said first time period.

30. The apparatus according to claim 29 wherein said indicator provides at least one of either a visual or audio indication.

31. The apparatus according to claim 28 wherein said controller is operative to cause said indication to be repeated responsive to a second occurrence, wherein said second occurrence corresponds to said sensed pressure not reaching said threshold level for a second time period, wherein said second time period is greater than said first time period.

32. The apparatus according to claim 31 wherein said controller is operative to change said valve to the second condition and maintain the valve in the second condition continuously responsive to a third occurrence, wherein said third occurrence corresponds to said sensed pressure not reaching said threshold level for a third time period, wherein said third time period is greater than said first time period.

33. The apparatus according to claim 1 and further comprising a dual cannula, wherein said dual cannula extends in a patient's nasal passage, and wherein said sensing passage and said delivery passage are in continuous fluid connection with such a patient's nasal passage through said dual cannula at all times throughout the respiration cycle of such a patient.

34. The apparatus according to claim 1 and further comprising a power source, and wherein said valve comprises a solenoid wherein said solenoid has a power rating, and wherein said controller is operative to cause power from said power source to be delivered to said solenoid to change said valve from said first condition to said second condition, and wherein to change said valve from the first condition to the second condition said controller is operative to cause a power signal to be delivered to said solenoid at a level above said power rating.

35. The apparatus according to claim 34 wherein after said valve is changed to the second condition said controller is operative to maintain said valve in the second condition by pulse width modulation of the power signal.

36. The apparatus according to claim 35 wherein said power source comprises a battery, whereby said pulse width modulation of said power signal extends battery life.

37. A method for delivering supplemental oxygen to a patient from a supply while conserving said supply, comprising the steps of:

providing oxygen from a supply to an inlet of a conserving apparatus;

sensing with a pressure sensor in the conserving apparatus when a sensed pressure corresponding to a nasal pressure in a nasal passage of a patient, reaches a threshold level;

delivering oxygen from an outlet from said conserving apparatus to the nasal passage of the patient for a delivery period responsive to the sensed pressure reaching the threshold level; and manually setting a manually actuated switch in connection with the conserving apparatus, wherein subsequent to setting said switch to a first switch position said sensing and delivery steps are executed, and wherein subsequent to setting said switch to a second switch position oxygen continuously flows from said outlet of said conserving device.

38. The method according to claim 37 and further comprising the step of controlling with a controller in the conserving apparatus the institution of the delivery step.

39. The method according to claim 38 wherein said controlling step includes determination of a quantity corresponding to an elapsed time since said sensed pressure reached the threshold level.

40. The method according to claim 38 wherein said controlling step includes determination of a quantity corresponding to an elapsed time said sensed pressure has been above said threshold level.

41. The method according to claim 38 wherein said controlling step includes determination of a quantity corresponding to an elapsed time since oxygen was last delivered from said outlet.

42. The method according to claim 38 wherein said controlling step includes execution of a fuzzy logic program.

43. The method according to claim 37 and further comprising prior to said delivering step, the step of calculating the delivery period with a controller.

44. The method according to claim 43 wherein said delivery period is calculated as a function of a first quantity corresponding to a time said sensed pressure was at least as low as said threshold level during an inhalation cycle of the patient immediately proceeding a current inhalation cycle.

45. The method according to claim 43 and further comprising prior to said delivering step, the step of inputting into an input device of said conservation apparatus a variable input value, and wherein said delivery period is calculated as a function of a quantity corresponding to said variable input value.

46. The method according to claim 44 and prior to said delivering step further comprising the step of inputting to an input device in said conservation apparatus a variable input value, and wherein said delivery period is calculated as a function of both said first quantity and a second quantity corresponding to said variable input value.

47. The method according to claim 37 wherein said providing step comprises setting a flow rate from said supply at a prescribed flow rate by adjusting a regulator in fluid connection with said oxygen supply.

48. The method according to claim 38 wherein said delivering step includes opening a valve, and wherein the step of moving said manual switch includes mechanically engaging said switch and said valve to open said valve.

49. The method according to claim 37 wherein said conserving apparatus further comprises a battery power source, and further comprising a low battery condition detecting device in operative connection with said battery power source and an indicator device, and wherein said method further comprises the step of providing an indication with said indicator device each time said delivery step is executed, and giving with said indicator a first indication when a low battery condition is detected, and giving a second indication when a low battery condition is not detected.

50. The method according to claim 37 wherein said delivering step comprises opening a solenoid valve, wherein delivery of oxygen occurs when said valve is open, and wherein said valve includes a solenoid having a power rating, and wherein said opening step comprises delivering a power signal above said power rating.

51. The method according to claim 50 wherein said delivering step further comprises after said opening step, the step of holding said valve open for said delivery period, and wherein said holding open step includes the step of pulse width modulating said power signal.

52. The method according to claim 37 and wherein said conserving apparatus comprises an indicator, and prior to said delivering step further comprising the steps of measuring a quantity corresponding to an elapsed time since said sensed pressure reached said threshold level, and giving an indication with said indicator when said quantity reaches an amount, whereby said indication is given when a time period has elapsed without said sensed pressure having reached said threshold level.

53. The method according to claim 37 and prior to said delivering step further comprising the step of measuring a quantity corresponding to an elapsed time since said sensed pressure reached said threshold level and delivering oxygen continuously from said outlet when said quantity reaches an amount, whereby oxygen is delivered continuously when a time period has elapsed without said sensed pressure having reached said threshold level.

54. An apparatus for conserving oxygen being delivered from an oxygen supply to a patient comprising:

a sensing passage fluidly connectable to a nasal passage of a patient, and a delivery passage separated from said sensing passage, wherein said delivery passage is fluidly connectable to the nasal passage of the patient;

a valve, wherein said valve includes a valve inlet, wherein said valve inlet is fluidly connectable to an oxygen supply, and wherein said valve further includes a valve outlet, wherein said valve outlet is fluidly connectable to said delivery passage, and wherein said valve is selectively changeable between a first valve condition wherein said valve inlet and valve outlet are not in fluid communication, and a second valve condition wherein said valve inlet and valve outlet are in fluid communication;

a pressure sensor, wherein said pressure sensor is in fluid communication with said sensing passage, and wherein said sensor is operative to a sense a sensed pressure in said sensing passage;

a controller in operative connection with said pressure sensor and said valve, wherein said controller is operative to cause said valve to change from the first condition to the second condition responsive to said sensed pressure reaching a threshold level, wherein said controller is operative to maintain said valve in the second condition for a variable delivery period each time said valve changes from said first condition to said second condition an input device, wherein said input device accepts a variable input value, and wherein said controller calculates said delivery period as a function of said input value, wherein said delivery period for a current inhalation cycle of a patient is calculated by said controller as a first function which includes a product of said variable input value and a time quantity, wherein said time quantity is calculated as a second function of a prior time value corresponding to a time said sensed pressure was at least as low as said threshold level during an immediately proceeding inhalation cycle.

\* \* \* \* \*